United States Patent [19]

Sullivan

[11] 4,367,337

[45] Jan. 4, 1983

[54] PROCESS FOR CONVERSION OF BENZIMIDAZOLONES TO BENZOTRIAZOLES

[75] Inventor: Frederick W. Sullivan, Flossmoor, Ill.

[73] Assignee: The Sherwin-Williams Company, Cleveland, Ohio

[21] Appl. No.: 222,446

[22] Filed: Jan. 5, 1981

[51] Int. Cl.$^3$ .......................................... C07D 249/18
[52] U.S. Cl. .................................. 548/257; 548/260; 548/305
[58] Field of Search ............................... 548/257, 305

[56] References Cited

U.S. PATENT DOCUMENTS

| | | | |
|---|---|---|---|
| 2,861,078 | 11/1958 | Miller and Schlaudecker | 260/308 |
| 3,227,726 | 1/1966 | Levy | 260/308 |
| 3,564,001 | 2/1971 | Long | 548/257 |
| 3,732,239 | 5/1973 | Spatz et al. | 260/308 B |
| 3,970,667 | 7/1976 | Gengnagel | 548/257 |
| 4,138,568 | 2/1979 | Hari et al. | 548/305 |
| 4,269,989 | 5/1981 | Heise et al. | 548/305 |

FOREIGN PATENT DOCUMENTS

| | | | |
|---|---|---|---|
| 713568 | 7/1965 | Canada | 548/305 |
| 1291509 | 3/1962 | France | 548/305 |

OTHER PUBLICATIONS

Elderfield, Robt., *Heterocyclic Compounds*, pp. 267–268, 285.

Damshroder et al.; *Organic Synthesis*, vol. 20, pp. 16–18; London, (1940).

Gabriello et al., *Chem. Abst.* 84: 164777u.

*Primary Examiner*—Donald G. Daus
*Assistant Examiner*—G. Hendrick
*Attorney, Agent, or Firm*—Robert E. McDonald; James V. Tura

[57] ABSTRACT

This invention relates to a process for producing triazoles which comprises effecting a mixture in an aqueous medium of at least one benzimidazolone and one or more nitrites and heating the mixture to temperatures ranging up to about 350° C. while maintaining pressures at levels sufficient to keep effective amounts of water present for the reaction.

10 Claims, No Drawings

PROCESS FOR CONVERSION OF BENZIMIDAZOLONES TO BENZOTRIAZOLES

BACKGROUND OF THE INVENTION

This invention relates to a novel process for the production of triazoles. More particularly, this invention relates to a process for the production of triazoles which involves reacting at least one benzimidazolone and at least one nitrite in the presence of water under conditions of elevated temperature and pressures.

SUMMARY OF THE PRIOR ART

Triazoles, especially benzotriazole and tolyltriazole, have found widespread application as corrosion inhibitors, chemical intermediates, catalysts, photographic chemicals and biocides.

Use of diazotization reactions to produce triazoles is known in the prior art. For example, U.S. Pat. No. 2,861,078 teaches the reaction of orthodiamines with nitrous acid to produce benzotriazoles. These prior art methods, however, have several drawbacks. Aromatic diamines are typically toxic and hazardous to handle. In addition, these diazotizations typically require the addition of an equivalent amount of an acid reacting substance such as sulfuric acid, acetic acid and the like, to the aqueous nitrite solution. The acid reacting substances typically used are relatively expensive, they can react with the nitrites to produce nitrous oxide gases which cause air pollution, and they can cause side reactions such as diazo coupling. The method of this invention, however, involves using a benzimidazolone rather than the more hazardous aromatic diamine as a starting material. Further, by effecting a mixture in an aqueous medium of the benzimidazolone and nitrite and maintaining or reacting said mixture at temperatures ranging up to about 350° C. under increased pressure, there is no need for the addition of an equivalent amount of an acid reacting substance. Therefore, by the teachings of this invention, the handling problems associated with aromatic diamines and the expense, handling problems and side reactions caused by the addition of acid can be avoided.

BRIEF SUMMARY OF THE INVENTION

It is an object of this invention to provide an improved process for the preparation of triazoles. Another object of this invention is to provide a process for the preparation of triazoles which involves maintaining a reaction at temperatures ranging up to about 350° C. and at pressures higher than atmospheric pressure. A further object of this invention is to provide an improved process for the preparation of benzotriazoles from benzimidazolones. Another object of this invention is to provide a process involving the nitrosation of benzimidazolones which avoids the cost and handling problems involved in the use addition of equivalent amounts of acids during the reaction. These and other objects of the invention will become apparent from the description and examples which follow.

This invention involves a process for producing triazoles which comprises mixing in the presence of water reactive amounts of (a) at least one benzimidazolone and (b) at least one nitrite and heating the aqueous mixture at temperatures ranging up to about 350° C. and at pressures sufficient to maintain liquid water in the reaction. For purposes of this disclosure, reactive amounts means essentially equimolar ratios of nitrite to benzimidazolone and in particular between about 0.8 and 1.2 moles of nitrite for each mole of benzimidazolone. Especially preferred is a level of about 1.00 to 1.1 moles of nitrite for each mole of benzimidazolone.

DETAILED DESCRIPTION OF THE INVENTION

The process described herein can be illustrated in general by the following equation (using sodium nitrite as the nitrite):

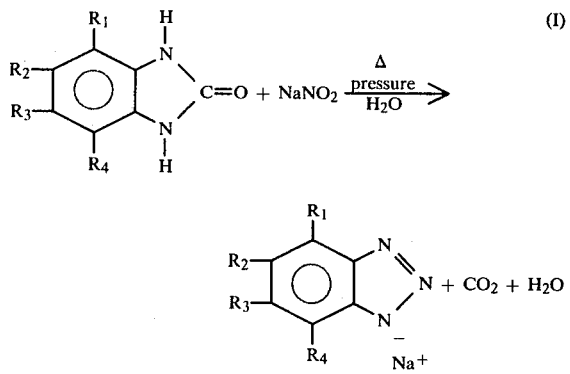

The triazoles produced by this process are initially in the form of the water soluble salt, (e.g. when sodium nitrite is used the sodium salt is produced), and they can be used in that form or, alternatively, the product can be acidified to a pH of about 6 or less thereby producing the protonated form of the triazole. The triazole can then be purified if desired, by recrystallization, or other methods known in the art.

The benzimidazolones useful in the practice of this invention have the following structure:

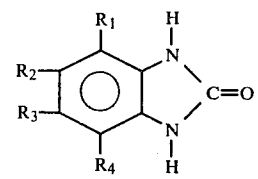

wherein $R_1$, $R_2$, $R_3$ and $R_4$ can be the same or different and are selected from the group consisting of hydrogen, alkyl, alkoxy, aryl, aroxy, aralkyl, aralkoxy, alkaroxy, halogen and nitro and wherein two or more of the groups could be part of a fused ring structure. Examples of such known benzimidazolones include 2-benzimidazolone, 5-methyl-2-benzimidazolone, 5-chloro-2-benzimidazolone, 5-methoxy-2-benzimidazolone and others. Especially preferred in the practice of this invention is 2-benzimidazolone or a methyl substituted 2-benzimidazolone because these can be used to produce benzotriazole and tolytriazole which are the triazoles of greatest commercial importance.

In general, any nitrite can be employed in the production of triazoles according to the process of this invention. Metal or inorganic nitrites are the preferred class of nitrites for this invention and especially preferred are the alkali metal nitrites because of their water solubility, availability and relatively low cost. Especially preferred in the practice of this invention is sodium nitrite.

As previously mentioned, between about 0.8 and 1.2 moles of sodium nitrite should be used for each mole of benzimidazolone. However, in order to drive the reaction to completion, it is preferred that at least about one mole of nitrite be used for each mole of the benzimidazolone and it is especially preferred to use the nitrite in about a 5 to 10% excess over equimolar proportions.

Since the process of this invention does not involve the creation of nitrous acid by the external addition of an equivalent amount of acid to the nitrate, the reaction must be maintained at temperatures which are higher than those of a typical diazotization reaction. The reaction in accordance with this process can be conducted at temperatures ranging up to about 350° C. although the preferred range for reaction is between about 100° C. and 350° C. and especially preferred is between about 180° C. and 300° C. Temperatures above about 300° C. could cause degradation of the triazoles produced if the temperature were maintained for too long a time and reaction rates at temperatures less than about 180° C. are relatively slow.

Although it is not our intent to be bound by theory, it is believed that the reaction as described in Equation (I) is self-catalytic. That is because some of the carbon dioxide produced as a by-product of the reaction is available to react with the salt of the triazole to produce the protonated form of the triazole. (For example, when sodium nitrite is used, the carbon dioxide reacts with the sodium salt of the triazole to produce soda ash and the protonated form of the triazole.) The free triazole is then able to act as a weak acid catalyst for the reaction.

If desired, catalytic amounts (e.g. about 0.5 to 2.0% by weight of the benzimidazolone) of weak to moderate organic acids, that is, those organic materials having a $K_a$ between about $10^{-9}$ and $10^{-1}$ and especially between $10^{-9}$ and $10^{-5}$, could be used to increase the rate of the reaction.

In order to assure complete reaction of the benzimidazolone and the nitrite, there must be enough water present in the system to provide for the solubility of the reactants. For ease of handling, it is generally preferred to use about 1.5 to 4.5 parts by weight of water for each part by weight of the nitrite, but greater or lesser amounts of water are also effective. Since at least enough liquid water to provide solubility for the reactants is essential for this reaction and since the reaction temperatures are often above the normal boiling point of water, it is essential to maintain pressure above atmospheric pressure within the reaction vessel during the course of this reaction. The pressure must be sufficiently high to prevent the vaporization of so much of the water available that solubility of the reactants can no longer be maintained. These pressures can be conveniently maintained by using a closed reaction vessel which can withstand high internal pressures and by adding sufficient quantities of the reactants so that the free volume within the reaction chamber is so limited that as water is vaporized, it increases the pressure within the reaction chamber to such a level that liquid water can be maintained in equilibrium with the vapor phase. Under typical reaction conditions of this invention the pressure inside the reaction vessel would be above about 70 psi and would typically be between 70 psi and 1,000 psi depending upon the reaction temperature, the size of the reaction vessel and the free volume within the reaction chamber.

DESCRIPTION OF THE PREFERRED EMBODIMENTS

The following examples have been selected to illustrate specific embodiments and practices of advantage to a more complete understanding of the invention.

EXAMPLE 1

0.50 grams 2-benzimidazolone, 0.257 grams sodium nitrite and 2.0 grams distilled water were sealed in a stainless steel pressure bomb reactor (5 inches long, ½ inch outside diameter) and immersed in a sand bath at 300° C. for fifteen minutes. The bomb was then cooled and opened releasing pressure. The red-brown liquid reaction product was rinsed from the bomb with distilled water forming a milky solution with a pH of 9.2. The solution was diluted to about 40 mls and acidified with dilute hydrochloric acid to a pH of about 2.4 producing a small amount of a brown precipitate. The precipitate was filtered off and discarded. The yellow filtrate liquid was extracted three times with 15 milliliters of methylene chloride and the methylene chloride extracts were reduced to dryness on a rotary evaporator yielding 0.21 grams of a yellow brown solid shown by IR to be 1,2,3-benzotriazole. The aqueous portion was brought back to a pH of 6-7 by the addition of dilute sodium hydroxide and again extracted with methylene chloride. This extraction yielded an additional 0.06 grams of 1,2,3-benzotriazole. The total yield in this case was about 61% of the theoretically optimum yield. This yield is lower than would be expected and is probably due to loss of liquid product upon the rapid release of pressure when the bomb was opened.

EXAMPLE 2

The reaction described in Example 1 was repeated except the reaction was held at only 250° C. for fifteen minutes. The red-brown liquid reaction product was rinsed from the bomb with distilled water and reduced in pH from 9 to about 6.5 by the addition of dilute hydrochloric acid. This solution was extracted four times with fifteen milliliters of methylene chloride and the methylene chloride extracts were reduced to dryness on a rotary evaporator. 0.33 grams of a reddish-brown solid, which analysis by infrared identified as 1,2,3-benzotriazole, was recovered. The aqueous portion left from the original extraction was evaporated to dryness and the solid produced was mixed with methylene chloride and filtered. The methylene chloride portion was reduced to dryness yielding approximately an additional 0.08 grams of 1,2,3-benzotriazole. The total yield of benzotriazole was about 93% of the theoretical optimum yield.

EXAMPLE 3

Into a two-liter autoclave fitted with a magnetic stirrer, cooling coils, sampling valve, pressure gauge, rupture disk and heating mantle was charged 216 grams (1.61 moles) 2-benzimidazolone, 116.6 grams (1.69 moles) of sodium nitrite, 374 grams of distilled water and 0.16 grams of sodium borohydride. The autoclave head was bolted into place and the reactants heated to a temperature of about 190° C. over a period of about 75 minutes. The reactants were held at this temperature and the corresponding pressure of about 260 psi for about three hours and then cooled by passing water through the cooling coils.

The products were diluted with about one liter of water and acidified to 5.5 pH by the addition of sulfuric acid. The oily layer which separated was removed and the water layer was extracted several times with ether. The ether and oily phase were combined and the ether removed by use of a rotary evaporator. Analysis of the product indicated it was 1,2,3-benzotriazole. The total amount of 1,2,3-benzotriazole obtained from the reaction was 163.5 grams or about 85.3% of the optimum theoretical yield.

The foregoing examples are merely illustrative and although this invention has been described by several specific embodiments, it is obvious that other variations and modifications can be made without departing from the spirit and scope of the invention as set forth in the appended claims.

The invention claimed is:

1. A process for producing triazoles consisting essentially of mixing in the presence of water reactive amounts of:

(a) at least one benzimidazolone having the structure:

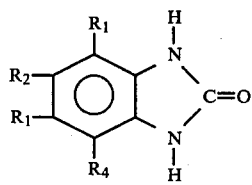

wherein $R_1$, $R_2$, $R_3$ and $R_4$ are the same or different and are selected from the group consisting of hydrogen, alkyl, alkoxy, aryl, aroxy, aralkyl, aralkoxy, alkaroxy, and halogen wherein 'aryl' or 'ar-' is defined as phenyl; and (b) at least one alkali metal nitrite; and heating the aqueous mixture at temperatures ranging from about 100° C. to 350° C. at pressure sufficient to maintain liquid water in the reaction.

2. The process of claim 1 further characterized in that the pressures are maintained at levels sufficient to have enough liquid water to solubilize the benzimidazolone and nitrite.

3. The process of claim 1 further characterized in that the nitrite is sodium nitrite.

4. The process of claim 1 further chracterized in that at least one mole of nitrite is present for each mole of benzimidazolone.

5. The process of claim 4 further characterized in that between about 1.00 and 1.1 moles of nitrite are present for each mole of benzimidazolone.

6. The process of claim 1 further characterized in that the pressure ranges above about 70 psi during the reaction.

7. The process of claim 1 further characterized in that the pressure is between about 70 psi and 1000 psi during the reaction.

8. The process of claim 1 further characterized in that the temperature of the reaction ranges between about 180° to about 300° C.

9. The process of claim 1 further characterized in that the benzimidazolone is 2-benzimidazolone.

10. The process of claim 1 further characterized in that the benzimidazolone is 5-methyl-2-benzimidazolone.

* * * * *